US012642972B2

(12) United States Patent
Kelley et al.

(10) Patent No.:    US 12,642,972 B2
(45) Date of Patent:        Jun. 2, 2026

(54) PERIPHERAL NERVE AND SPINAL CORD DIFFERENTIAL TARGET MULTIPLEXED STIMULATION

(71) Applicant: Medtronic, Inc., Minneapolis, MN (US)

(72) Inventors: Brooke G. Kelley, Brooklyn Center, MN (US); Juan G. Hincapie, Maple Grove, MN (US); Andrew J. Cleland, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 328 days.

(21) Appl. No.: 18/546,765

(22) PCT Filed: Feb. 24, 2022

(86) PCT No.: PCT/US2022/017683
§ 371 (c)(1),
(2) Date: Aug. 16, 2023

(87) PCT Pub. No.: WO2022/182860
PCT Pub. Date: Sep. 1, 2022

(65) Prior Publication Data
US 2024/0131343 A1      Apr. 25, 2024
US 2024/0226573 A9      Jul. 11, 2024

Related U.S. Application Data

(60) Provisional application No. 63/153,029, filed on Feb. 24, 2021.

(51) Int. Cl.
*A61N 1/36*              (2006.01)
(52) U.S. Cl.
CPC ..... *A61N 1/36171* (2013.01); *A61N 1/36062* (2017.08); *A61N 1/36178* (2013.01)

(58) Field of Classification Search
CPC .............. A61N 1/0551; A61N 1/36062; A61N 1/36071; A61N 1/36128; A61N 1/36139;
(Continued)

(56) References Cited

U.S. PATENT DOCUMENTS

2010/0249875 A1*  9/2010  Kishawi ............. A61N 1/36021
                                                                            607/46
2011/0054565 A1*  3/2011  Wacnik ............. A61N 1/36185
                                                                            607/46
(Continued)

FOREIGN PATENT DOCUMENTS

WO          2011019933 A1      2/2011

OTHER PUBLICATIONS

International Preliminary Report on Patentability from International Application No. PCT/US2022/017683 dated Sep. 7, 2023, 7 pp.
(Continued)

*Primary Examiner* — Amanda K Hulbert
(74) *Attorney, Agent, or Firm* — Shumaker & Sieffert, P.A.

(57)                    ABSTRACT

Devices, systems, or methods include generating, by stimulation generation circuitry, a first train of electrical stimulation pulses at a first frequency to a first target tissue; and generating, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second tram of electrical stimulation pulses. At least the first target tissue is associated with a spinal cord of a patient, and the second target tissue is associated with at least one of a peripheral nerve or a nerve root of the patient.

23 Claims, 10 Drawing Sheets

(58) Field of Classification Search
CPC ............ A61N 1/36164; A61N 1/36171; A61N
1/36178; A61N 1/37288
See application file for complete search history.

(56) References Cited

U.S. PATENT DOCUMENTS

| | | |
|---|---|---|
| 2014/0277281 A1 | 9/2014 | Grandhe |
| 2017/0361103 A1 | 12/2017 | Hadjiyski |
| 2020/0353256 A1 | 11/2020 | Vallejo et al. |

OTHER PUBLICATIONS

International Search Report and Written Opinion of International
Application No. PCT/US2022/017683, dated May 30, 2022, 13 pp.

* cited by examiner

300

700

DELIVER STIMULATION VIA ELECTRODE
COMBINATION AT FIRST LOCATION

702

DETECT ECAP VIA ELECTRODE
COMBINATION AT SECOND LOCATION

704

DETERMINE, BASED ON A TIMING OF
ECAP DETECTION, TIMING OF DELIVERY
OF BASE PULSES AND PRIME PULSES

PERIPHERAL NERVE AND SPINAL CORD DIFFERENTIAL TARGET MULTIPLEXED STIMULATION

This application is a national stage entry of International Patent Application No. PCT/US2022/017683, filed Feb. 24, 2022, which claims priority to and the benefit of U.S. Provisional Patent Application 63/153,029, entitled "PERIPHERAL NERVE AND SPINAL CORD DIFFER-ENTIAL TARGET MULTIPLEXED STIMULATION" and filed on Feb. 24, 2021, the entire contents of application nos. PCT/US2022/017683 and 63/153,029 are incorporated herein by reference.

TECHNICAL FIELD

This disclosure generally relates to medical devices, and more specifically, electrical stimulation.

BACKGROUND

Medical devices may be external or implanted and may be used to deliver electrical stimulation therapy to patients via various tissue sites to treat a variety of symptoms or con-ditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, the disclosure is directed to devices, systems, and techniques for providing therapy to a patient (e.g., pain relief therapy) by using differential target multiplexed (DTM) stimulation at multiple tissue sites to activate mul-tiple mechanisms to provide pain relief, such as neuronal and glial cells. For example, the DTM stimulation may include delivering first stimulation at a first frequency to a first target tissue and delivering second stimulation at a second frequency to a second target tissue different from the first target tissue. The first tissue site may be located near the spinal cord, and the second tissue site may be located near a peripheral nerve or nerve root. The first stimulation and the second stimulation may be interleaved over time such that one or more pulses from the first stimulation alternate with one or more pulses from the second stimulation.

In one example, this disclosure describes a method includes generating, by stimulation generation circuitry, a first train of electrical stimulation pulses at a first frequency to a first target tissue; and generating, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some elec-trical stimulation pulses of the second train of electrical stimulation pulses; wherein at least the first target tissue is associated with a spinal cord of a patient, and the second target tissue is associated with a peripheral nerve of the patient.

In another example, this disclosure describes a method includes generating, by stimulation generation circuitry, a first train of electrical stimulation pulses at a first frequency to a first target tissue; and generating, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some elec-trical stimulation pulses of the second train of electrical stimulation pulses; wherein at least the first target tissue is associated with at least one of a peripheral nerve or a nerve root of a patient, and the second target tissue is associated with a spinal cord of the patient.

In another example, this disclosure describes a medical device includes processing circuitry configured to: generate, by stimulation generation circuitry, a first train of electrical stimulation pulses at a first frequency to a first target tissue; and generate, by the stimulation generation circuitry, a second train of electrical stimulation pulses at a second frequency to a second target tissue different from the first target tissue; wherein at least some electrical stimulation pulses of the first train of electrical stimulation pulses are interleaved with at least some electrical stimulation pulses of the second train of electrical stimulation pulses; wherein at least the first target tissue is associated with a spinal cord of a patient, and the second target tissue is associated with at least one of a peripheral nerve or a nerve root of the patient.

In another example, this disclosure describes a medical device includes processing circuitry configured to: generate, by stimulation generation circuitry, a first train of electrical stimulation pulses at a first frequency to a first target tissue; and generate, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses; wherein at least the first target tissue is associated with a spinal cord of a patient, and the second target tissue is associated with at least one of a peripheral nerve or a nerve root of the patient.

In another example, this disclosure describes a medical device includes processing circuitry configured to: generate, by stimulation generation circuitry, a first train of electrical stimulation pulses at a first frequency to a first target tissue; and generate, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses; wherein at least the first target tissue is associated with at least one of a peripheral nerve or a nerve root of a patient, and the second target tissue is associated with a spinal cord of the patient.

In another example, this disclosure describes a computer-readable storage medium includes generate, by stimulation generation circuitry, a first train of electrical stimulation pulses at a first frequency to a first target tissue; and generate, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses; wherein at least the first target tissue is associated with a spinal cord of a patient, and the second target tissue is associated with at least one of a peripheral nerve or a nerve root of the patient.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1A:
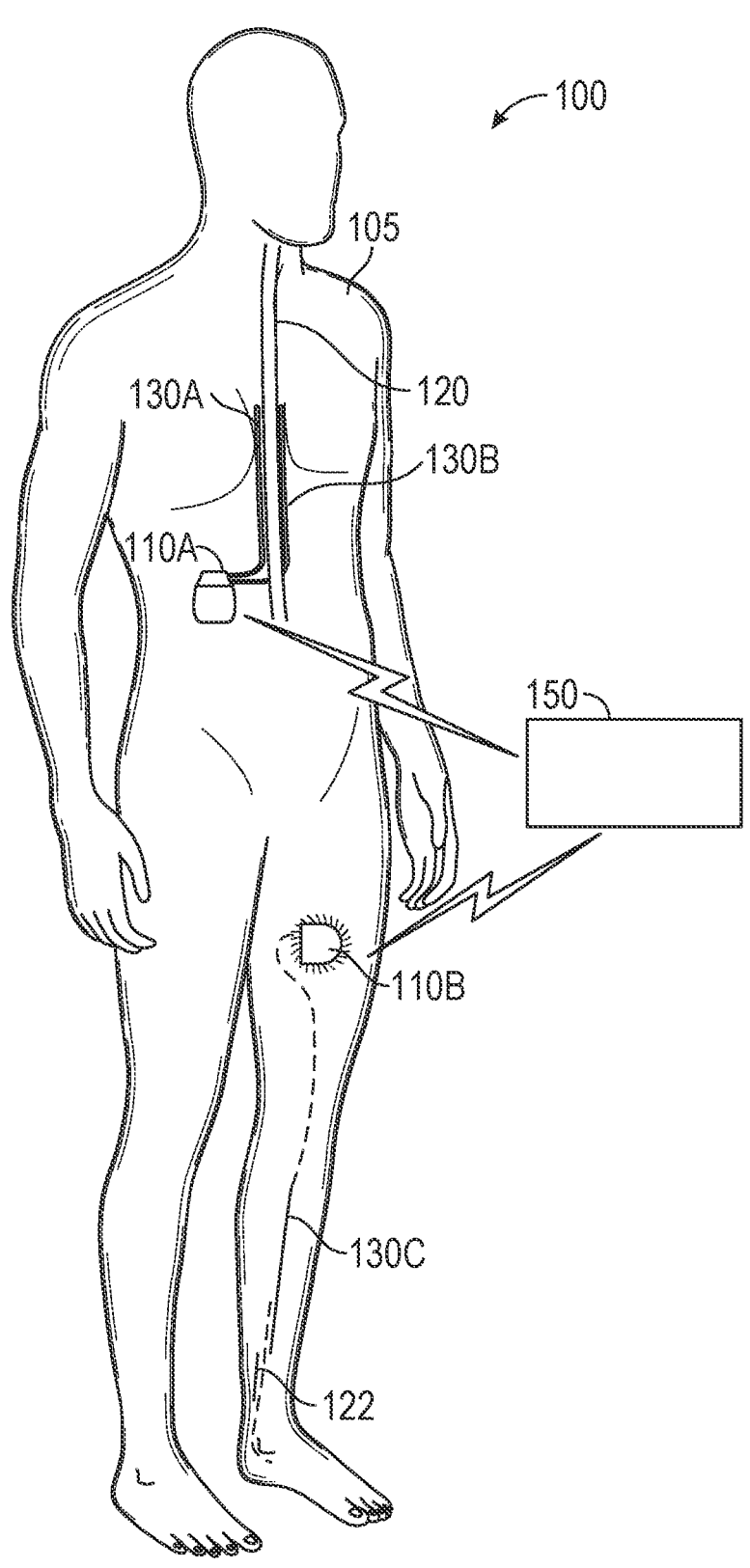
FIG. 1A is a conceptual diagram illustrating an example system that includes an implantable medical device (IMD) configured to deliver spinal cord stimulation (SCS) therapy and peripheral nerve stimulation (PNS) and an external programmer, in accordance with one or more techniques of this disclosure.

The disclosure describes examples of medical devices, systems, and techniques for providing therapy to a patient (e.g., pain relief therapy) by using DTM stimulation at two different tissue sites. For example, the disclosure may use DTM to provide stimulation at peripheral nerve or nerve root and at the spinal cord. The signals at the spinal cord and/or near the nerve may by subthreshold (e.g., below perception threshold or the amplitude is less than perception threshold). The stimulation may provide focal pain relief and/or regional pain relief. In some examples, control of the therapy may occur in a closed loop system incorporating biological signals as a feedback variable such as, but not limited to, ECAP signals.

The oscillatory electromagnetic fields applied to neural structures induce changes in synaptic plasticity upon modulation of two different cell populations: Neurons and glial cells. This is concurrent with the effects on neurons such as action potential generation or blockade by the stimulation of mechanosensitive fibers to mask (or close the gate to) nociceptive signals travelling to the brain. In addition, glial cells are immunocompetent cells that constitute the most common cell population in the nervous system and play a fundamental role in the development and maintenance of chronic neuropathic pain. Glial cells are responsible for monitoring the status of the nervous system by using constant chemical communication with neurons and other glial cells. Microglia are the glial cells in charge of monitoring the brain and spinal cord. Following a nerve (or brain) injury, these cells become activated and respond to any stimulus that is considered a threat to Central Nervous System (CNS) homeostasis. This activation involves morphological changes in the microglia accompanied by changes in chemotaxis and phagocytic activity, as well as the release of chemokines and cytokines that induce a response from the immune system. It has been shown that microglia are the CNS immediate responders to injury. Injury also triggers the activation of astrocytes, glial cells that monitor the synaptic clefts and thus are involved in synaptic plasticity via the regulation of neuro and glial transmitter molecules and involvement of immune cells for synaptic pruning. Astrocyte activation and regulation is sustained for longer time and thus it can be hypothesized that astrocytes play an important role in changes affecting synaptic plasticity in chronic pain. There is experimental evidence that supports this hypothesis. It is worth noting that at the Peripheral Nervous System (PNS), oligodendrocytes, Schwann cells and satellite glial cells, similar to astroglia, play similar roles.

Calcium ions and phosphorylating processes mediated by ATP play an important role in glial response to injury. Electrical impulses induce changes in the concentration of calcium ions in the astrocytes, which propagates between astrocytes via calcium waves. This, in turn, signals the release of transmitters such as glutamate, adenosine and ATP, even after sodium channel blockade, which modulates both neuronal excitability and synaptic transmission. The presence of an external oscillatory electrical field then provides a stimulus for glial cells to affect synapses that have been negatively affected by injury. The electrical field provides a priming response that moves the function of the synapse towards a normal state.

It may be possible to electrically stimulate glial cells as their response (glial depolarization, release/uptake of ions, release of glial transmitters) depends on the specific parameters such as amplitude, frequency, phase polarity, waveform shape, and width (in the case of rectangular waveforms) of the stimulation. For example, the release of glutamate from astrocytes may be modulated in proportion to the amount of anodic current administered during biphasic pulsed stimulation. Monophasic cathodic stimulation of hippocampal astrocytes promotes the release of glutamate. The introduction of an anodic component decreases the amount of glutamate released. Given that the glial cells and neurons respond differently to electrical fields; it is then possible to differentially modulate the response of these cell populations with distinctly different electrical parameters. This theory sets a mechanistic basis of multimodal stimulation. Subthreshold stimulation with an electromagnetic field set at an optimum frequency, amplitude, waveform, width and phase may modulate the behavior of glial cells and the way they interact with neurons at the synaptic level. Thus, multimodal modulation provides the ability to control the balance of glutamate and glutamine in a calcium dependent manner and the possibility of modulating such balance in the appropriate manner with electromagnetic fields.

In the disclosed DTM stimulation technique, a mechanism of depolarization is combined with amplitudes lower or slightly higher than the Paresthesia Threshold (PT), so the patient may or may not experience tingling even though tonic stimulation is being applied. In certain embodiments, the composite signal, including the primary component that provides electrical stimulation at higher than the tonic frequencies, may activate the molecular mechanisms that allow for resetting of the synaptic plasticity to a state closer to the one previous to central sensitization induced by injury, thus providing a mechanism for long lasting pain relief.

In certain embodiments, the Priming Frequency (PF) may be set to any frequency between 900 Hz to 1200 Hz. According to embodiments, multiple signals can be multiplexed within a repeating set of N pulse spaces. Each pulse space within the pattern can correspond to a different electrical signal with respective parameters. The lower average frequency can be generated by multiplexing a second, tonic signal component in one of the N pulses. According to embodiments, the burst frequency of the priming frequency signal component can be an integer multiple (M) of the tonic signal frequency such that the tonic pulse space only includes a pulse every M times the N set of pulse spaces are repeated. The blank pulse space results in a burst of N−1 pulses at the "burst" frequency, followed by a "missed" pulse resulting in a lower "average" frequency over the set of N pulses. As used herein, the average frequency of the priming signal is calculated separate without including pulses associated with the tonic signal. In some embodiments, the priming signal can be delivered to a different physical location using a different set of electrodes relative to the tonic signal.

In further exemplary embodiments, a second or tonic component is set at a frequency of about 50 Hz, interleaved into the treatment to account for the average priming frequency, though other tonic values and ranges are contemplated herein, e.g., 10 Hz to 60 Hz.

Disclosed herein are apparatus and methods for managing pain in a patient by using multimodal stimulation of neural structures, with an electromagnetic signal having multiple components of characteristic frequencies, amplitudes, and phase polarities. Multimodal modulation for pain management, in accordance with the disclosure, contemplates the use of oscillating electromagnetic fields which is applied via an array of electrodes (referred as contacts or leads) to a particular neural structure using temporal and amplitude characteristics, to modulate glial and neuronal interactions as the mechanism for relieving chronic pain. More specifically, exemplary aspects provide an apparatus and method for modulating the expression of genes involved in diverse pathways including inflammatory/immune system mediators, ion channels and neurotransmitters, in both the Spinal Cord (SC) and Dorsal Root Ganglion (DRG). In one exemplary embodiment, such expression modulation is caused by spinal cord stimulation or peripheral nerve stimulation. In one embodiment, the amplitudes and frequencies of the signal or signals used to create the multimodal stimulation of neural structures may be optimized for pain relief and low power usage in an implantable multimodal signal generator, as described herein.

According to one exemplary embodiment, apparatuses and methods provide for managing pain in a patient by using multiplexed stimulation signals to target different neural structures such that the multiple stimulation signals are multiplexed in the time domain, hereafter referred to as "differential target multiplexed stimulation." For instance, a signal generator can multiplex signals that can have different signal characteristics (e.g., pulse frequency, amplitude, or pulse duration) to generate differential target multiplexed stimulation for pain management. In accordance with aspects of the disclosure, the output of the signal generator can be used to produce separate oscillating electromagnetic fields (stimulation signals, such as pulses or continuous signals) which can be applied to different set of a plurality of electrodes (also referred as contacts). The electrodes can be part of a lead that is designed to apply the respective stimulation signals to different parts of a particular neural structure.

Various aspects of the disclosure relate to the use of a variety of temporal and amplitude characteristics in order to modulate glial and neuronal interactions, for example, as the mechanism for relieving chronic pain. The multiplexed stimulation signals can have characteristics that allow for a synergistic targeting of glial cells and neurons in a differential manner. For instance, disclosed are embodiments relating to an apparatus and method for modulating the expression of genes and proteins involved in diverse pathways, including inflammatory/immune system mediators, ion channels and neurotransmitters, associated with the interaction of glia and neurons in neural tissue. In embodiments, such expression modulation may be caused by any of spinal cord stimulation, dorsal root ganglion stimulation, brain stimulation, or peripheral nerve stimulation. In some embodiments, the amplitudes, phase polarity, waveforms, and frequencies of the signals combined to create the differential target multiplexed stimulation of neural structures may be optimized for pain relief and low power usage in an implantable signal generator, as described herein.

In embodiments of differential target multiplexed stimulation therapy, a set of high frequency charge-balanced biphasic pulsed signals in which the polarity of the first phase of the high frequency signals may be either cathodic or anodic is utilized. In embodiments, a set of low frequency signals is used that may have waveform characteristics different from those of the high frequency signals. The polarity of the first phase of the biphasic charge-balanced low frequency signals may be either cathodic or anodic. The high and low frequency stimulation signals can be delivered to the neural tissues by multiplexing individual pulses from each via respective sets of electrodes. In certain embodiments, the respective sets of electrodes can be co-located in close proximity to the same neural tissue (e.g., near the same vertebrae).

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1A is a conceptual diagram illustrating example system 100 that includes a first implantable medical device (IMD) 110A configured to deliver stimulation to the spinal cord stimulation, a second implantable medical device (IMD) 110B configured to deliver stimulation to a peripheral nerve, processing circuitry 140 (FIG. 2), and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to implantable SCS and/or PNS systems for purposes of illustration for delivering the different stimulations described herein, but without limitation as to other types of medical devices or other therapeutic applications of medical devices. Instead of separate devices for delivering stimulation to the spinal cord and a peripheral nerve, a single device may be coupled to one or more leads carrying electrodes to each target location and/or one or more wireless devices configured to deliver stimulation to the target tissue site. In the example of a single device coupled to leads disposed at different locations, the timing of the delivery of the stimulus and the detection of an ECAP, such as detection of the ECAP at the lead different than the lead that delivered the stimulus, may be fixed based on the known distances along the leads. In other examples of a single device or multiple devices coupled to respective leads at different locations, one or both devices may communicate to determine the time required for the ECAP signal to propagate to the sensing location from the stimulus location. Then, the single device or multiple devices may coordinate delivery of the stimulus from one lead and the sensing window at the other lead in order to improve detection of the ECAP signal. This timing can be set initially or periodically over time if conduction changes or other issues occur. Example peripheral nerves include, but are not limited to, sacral nerve, tibial nerve, pudendal nerve, sciatic nerve, cluneal nerve, genicular nerve, occipital nerve, ulnar or radial nerve, or the dorsal rami of any spinal nerve. Other nerves may include the ilioinguinal, genitofemoral, lateral femoral cutaneous, suprascapular, or femoral nerve.

As shown in FIG. 1A, system 100 includes an IMD 110A, leads 130A and 130B, IMD 110B, lead 130C, and external programmer 150 shown in conjunction with a patient 105, who is ordinarily a human patient. In the example of FIG. 1A, IMD 110 is an implantable electrical stimulator that is configured to generate and deliver electrical stimulation therapy to patient 105 via one or more electrodes of electrodes of leads 130A and/or 130B, and 130C (collectively, "leads 130"), e.g., for relief of chronic pain or other symptoms. In other examples, IMD 110 may be coupled to a single lead carrying multiple electrodes or more than two leads each carrying multiple electrodes. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1A, leads 130A, 130B carry electrodes that are placed adjacent to the target tissue of spinal cord 120. In some examples, lead 130C carries electrodes that are placed adjacent to target tissue near peripheral nerve 122. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses are typically predetermined parameter values determined prior to delivery of the stimulation pulses (e.g., set according to a stimulation program). However, in some examples, system 100 changes one or more parameter values automatically based on one or more factors or based on user input.

Although FIG. 1A is directed to delivering stimulation to the spinal cord and to a peripheral nerve, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105. For example, for PNFS, one of the leads 130 is disposed along the spinal cord 120, and one of the leads is disposed along a peripheral nerve 122.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms and may include a first target tissue and a second target tissue. In some examples, the target tissue includes nerves, smooth muscle or skeletal muscle, or peripheral nerves. In the example illustrated by FIG. 1A, a first target tissue is tissue proximate spinal cord 120, such as within an intrathecal space or epidural space of spinal cord 120, or, in some examples, adjacent nerves that branch off spinal cord 120. In some examples, a second target tissue may include a tissue near a peripheral nerve 122, such as in a leg, for example, near a knee or ankle of a patient. Other peripheral nerves may be located at or near target tissue in the arm, neck, abdomen, pelvic floor, upon exiting the spinal cord, or any other location. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results. For example, as described herein, electrical stimulation may be directed to glial cells while other electrical stimulation (delivered by different electrode combination) is directed to neurons, such as peripheral nerves.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy. For example, external programmer 150 may transmit therapy stimulation programs, stimulation parameter adjustments, therapy stimulation program selections, user input, or other information to control the operation of IMD 110, e.g., by wireless telemetry or wired connection. As described herein, stimulation delivered to the patient may include control pulses, and, in some examples, stimulation may include control pulses and informed pulses.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and the two IMDs 110A, B. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130, and to a target tissue site of a peripheral nerve 122. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Optionally, pain relief may also be used by position the leads in the neighborhood of a peripheral nerve 122 in addition to positioning one of the leads near the spinal cord 120. Peripheral Nerve Stimulation (PNS) is an alternative therapy for chronic pain in which a target nerve has been identified to be the source of pain. The current understanding of the therapeutic effects of PNS is also based on the gate control theory. However, axons of sensory neurons in peripheral nerves are surrounded by glial cells that are known to respond accordingly to the frequency characteristics of a stimulus.

Figure 1B:
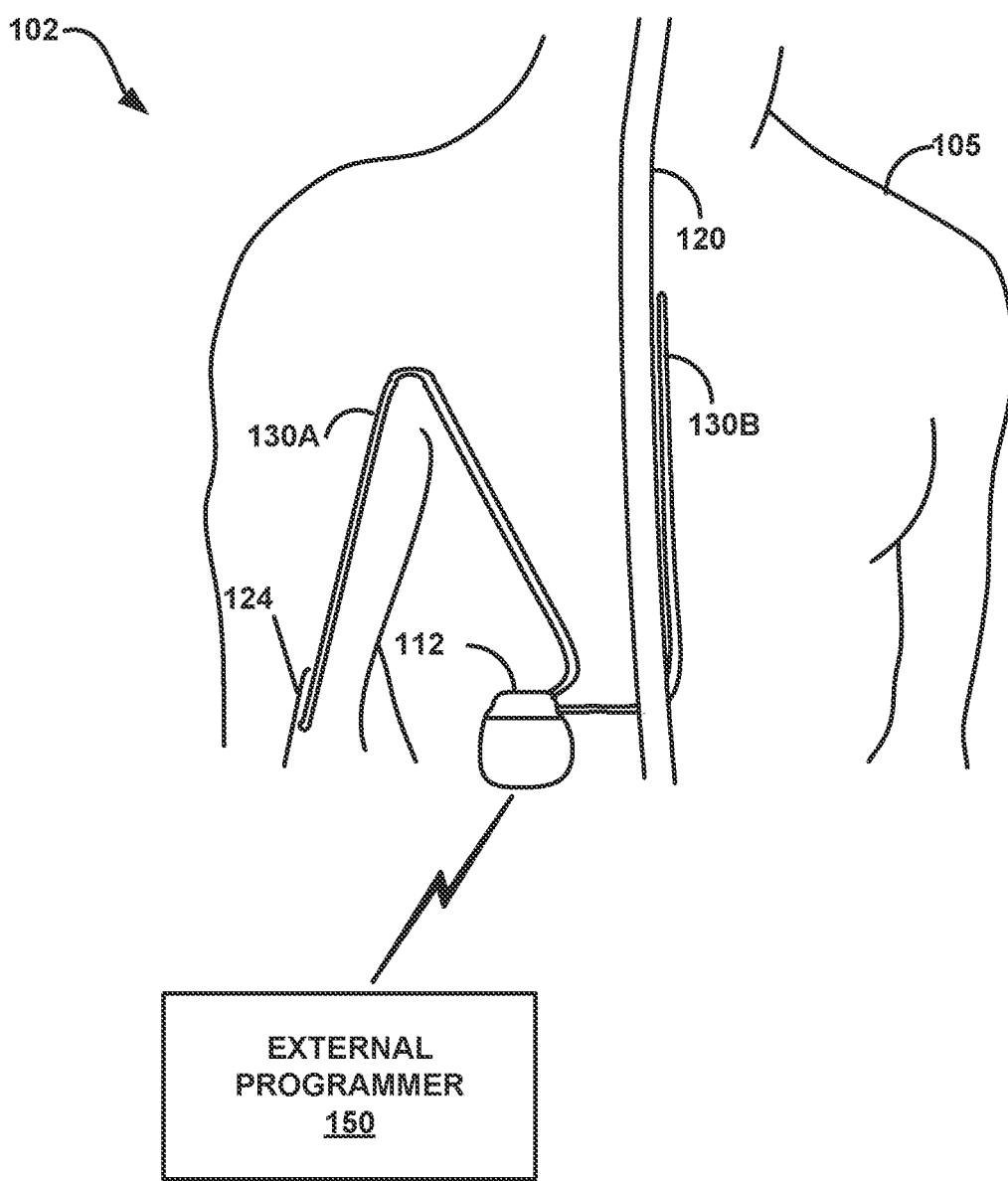
FIG. 1B is a conceptual diagram illustrating an example system that includes an implantable medical device (IMD) configured to deliver spinal cord stimulation (SCS) therapy and peripheral nerve stimulation (PNS) and an external programmer, in accordance with one or more techniques of this disclosure.

FIG. 1B is a conceptual diagram illustrating example system 102 that includes an implantable medical device (IMD) 112 configured to deliver spinal cord stimulation (SCS) therapy and peripheral nerve stimulation (PNS) therapy, processing circuitry 140 (FIG. 2), and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to implantable SCS and PNS systems for purposes of illustration, but without limitation as to other types of medical devices or other therapeutic applications of medical devices.

As shown in FIG. 1B, system 102 includes an IMD 112, leads 130A and 130B, and external programmer 150 shown in conjunction with a patient 105, who is ordinarily a human patient. In the example of FIG. 1B, IMD 112 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 112 may be coupled to a single lead carrying multiple electrodes or more than two leads each carrying multiple electrodes. IMD 112 may be a chronic electrical stimulator that remains implanted within patient 105 for weeks, months, or even years. In other examples, IMD 112 may be a temporary, or trial, stimulator used to screen or evaluate the efficacy of electrical stimulation for chronic therapy. In one example, IMD 112 is implanted within patient 105, while in another example, IMD 112 is an external device coupled to percutaneously implanted leads.

IMD 112 may be constructed of any polymer, metal, or composite material sufficient to house the components of IMD 112 (e.g., components illustrated in FIG. 2) within patient 105. In this example, IMD 112 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 112 may be implanted within other suitable sites within patient 105, which may depend, for example, on the target site within patient 105 for the delivery of electrical stimulation therapy. The outer housing of IMD 112 may be configured to provide a hermetic seal for components, such as a rechargeable or non-rechargeable power source. In addition, in some examples, the outer housing of IMD 112 is selected from a material that facilitates receiving energy to charge the rechargeable power source.

Electrical stimulation energy, which may be constant current or constant voltage-based pulses, for example, is delivered from IMD 112 to one or more target tissue sites of patient 105 via one or more electrodes (not shown) of implantable leads 130. In the example of FIG. 1B, lead 130B carries electrodes that are placed adjacent to the target tissue of spinal cord 120. In some examples, lead 130A carries electrodes that are placed adjacent to target tissue near peripheral nerve 124. One or more of the electrodes may be disposed at a distal tip of a lead 130 and/or at other positions at intermediate points along the lead. Leads 130 may be implanted and coupled to IMD 112. The electrodes may transfer electrical stimulation generated by an electrical stimulation generator in IMD 112 to tissue of patient 105. Although leads 130 may each be a single lead, lead 130 may include a lead extension or other segments that may aid in implantation or positioning of lead 130. In some other examples, IMD 112 may be a leadless stimulator with one or more arrays of electrodes arranged on a housing of the stimulator rather than leads that extend from the housing. In addition, in some other examples, system 102 may include one lead or more than two leads, each coupled to IMD 112 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 112 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses are typically predetermined parameter values determined prior to delivery of the stimulation pulses (e.g., set according to a stimulation program). However, in some examples, system 102 changes one or more parameter values automatically based on one or more factors or based on user input.

Although FIG. 1B is directed to a combination of stimulation delivered to the spinal cord and a peripheral nerve, e.g., used to treat pain, in other examples system 102 may be configured to treat any other condition that may benefit from electrical stimulation therapy. For example, system 102 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 102 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105. For example, for PNFS, one of the leads 130 is disposed along the spinal cord 120, and one of the leads is disposed along a peripheral nerve 124.

In some examples, lead 130 includes one or more sensors configured to allow IMD 112 to monitor one or more parameters of patient 105, such as patient activity, pressure, temperature, or other characteristics. The one or more sensors may be provided in addition to, or in place of, therapy delivery by lead 130.

IMD 112 is configured to deliver electrical stimulation therapy to patient 105 via selected combinations of electrodes carried by one or both of leads 130, alone or in combination with an electrode carried by or defined by an outer housing of IMD 112. The target tissue for the electrical stimulation therapy may be any tissue affected by electrical stimulation, which may be in the form of electrical stimulation pulses or continuous waveforms and may include a first target tissue and a second target tissue. In some examples, the target tissue includes nerves, smooth muscle or skeletal muscle, or peripheral nerves. In the example illustrated by FIG. 1B, a first target tissue is tissue proximate spinal cord 120 or tissue associated with spinal cord 120, such as within an intrathecal space or epidural space of spinal cord 120, or, in some examples, adjacent nerves that branch off spinal cord 120. In some examples, a first target tissue is a nerve root or peripheral nerve in the torso or within few inches of spinal cord 120. In some examples, a second target tissue may include a tissue near a peripheral nerve 124 or associated with a peripheral nerve, such as in an arm, for example, near an elbow or wrist of a patient. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results. For example, as described herein, electrical stimulation may be directed to glial cells while other electrical stimulation (delivered by different electrode combination) is directed to neurons, such as peripheral nerves.

IMD 112 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 112 according to that program. For example, a therapy stimulation program that controls delivery of stimulation by IMD 112 in the form of pulses may define values for voltage or current pulse amplitude, pulse width, and pulse rate (e.g., pulse frequency) for stimulation pulses delivered by IMD 112 according to that program.

A user, such as a clinician or patient 105, may interact with a user interface of an external programmer 150 to program IMD 112. Programming of IMD 112 may refer generally to the generation and transfer of commands, programs, or other information to control the operation of IMD 112. In this manner, IMD 112 may receive the transferred commands and programs from external programmer 150 to control electrical stimulation therapy. For example, external programmer 150 may transmit therapy stimulation programs, stimulation parameter adjustments, therapy stimulation program selections, user input, or other information to control the operation of IMD 112, e.g., by wireless telemetry or wired connection. As described herein, stimulation delivered to the patient may include control pulses, and, in some examples, stimulation may include control pulses and informed pulses.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 112, whereas a patient programmer may support adjustment and selection of such programs by a patient during ordinary use. In other examples, external programmer 150 may include, or be part of, an external charging device that recharges a power source of IMD 112. In this manner, a user may program and charge IMD 112 using one device, or multiple devices.

As described herein, information may be transmitted between external programmer 150 and IMD 112. Therefore, IMD 112 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 112 implant site to improve the quality or security of communication between IMD 112 and external programmer 150. Communication between external programmer 150 and IMD 112 may occur during power transmission or separate from power transmission.

In some examples, IMD 112, in response to commands from external programmer 150, delivers electrical stimulation therapy according to a plurality of therapy stimulation programs to a target tissue site of the spinal cord 120 of patient 105 via electrodes (not depicted) on leads 130, and to a target tissue site of a peripheral nerve 122. In some examples, IMD 112 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Optionally, pain relief may also be used by position the leads in the neighborhood of a peripheral nerve 122 in addition to positioning one of the leads near the spinal cord 120. Peripheral Nerve Stimulation (PNS) is an alternative therapy for chronic pain in which a target nerve has been identified to be the source of pain. The current understanding of the therapeutic effects of PNS is also based on the gate control theory. However, axons of sensory neurons in peripheral nerves are surrounded by glial cells that are known to respond accordingly to the frequency characteristics of a stimulus.

Figure 1C:
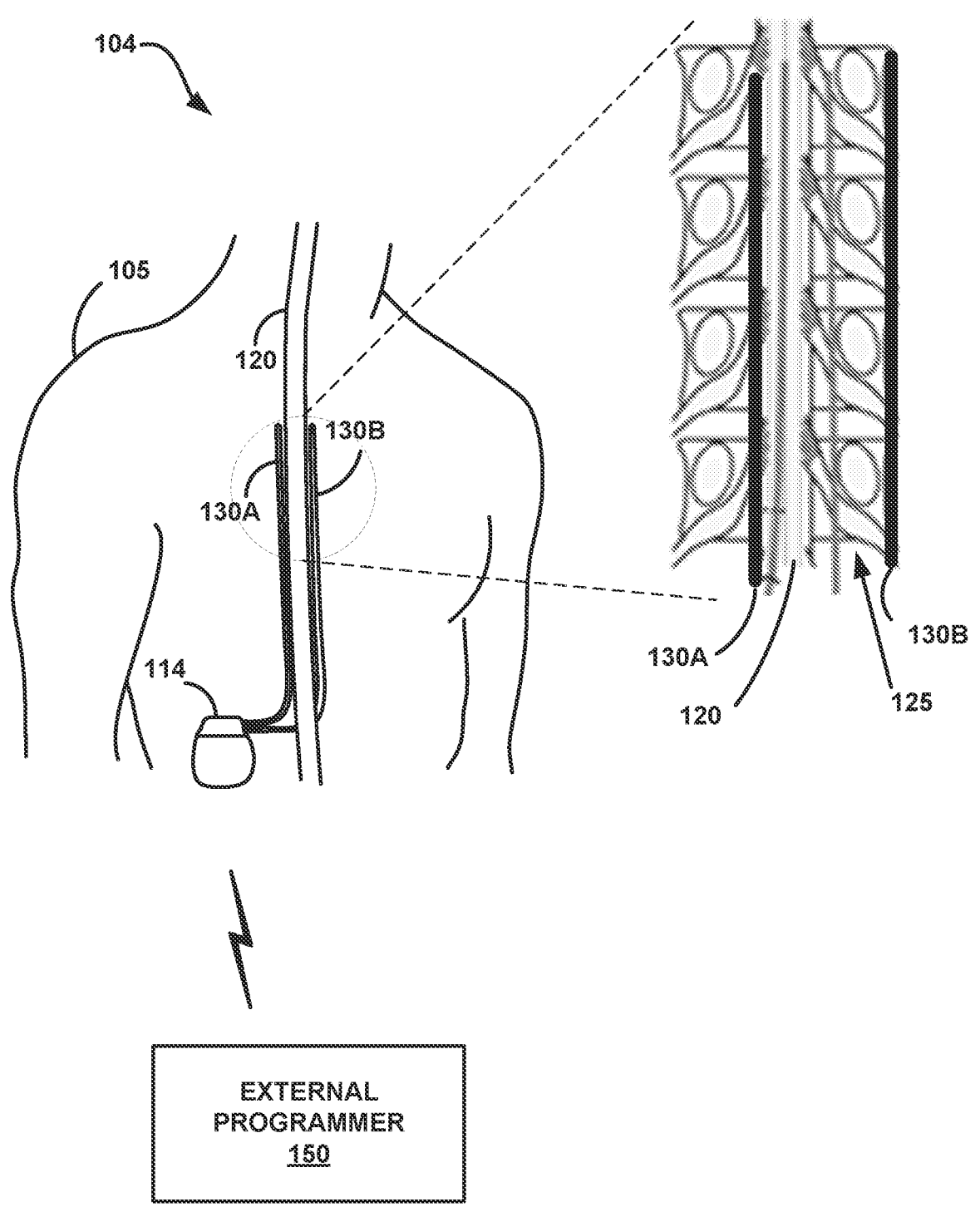
FIG. 1C is a conceptual diagram illustrating an example system that includes an implantable medical device (IMD) configured to deliver spinal cord stimulation (SCS) therapy and peripheral nerve stimulation (PNS) and an external programmer, in accordance with one or more techniques of this disclosure.

FIG. 1C is a conceptual diagram illustrating example system 104 that includes an implantable medical device (IMD) 114 configured to deliver spinal cord stimulation (SCS) therapy and peripheral nerve stimulation (PNS) therapy, processing circuitry 140 (FIG. 2), and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to implantable SCS and PNS systems for purposes of illustration, but without limitation as to other types of medical devices or other therapeutic applications of medical devices.

As shown in FIG. 1C, system 104 includes an IMD 114, leads 130A and 130B, and external programmer 150 shown in conjunction with a patient 105, who is ordinarily a human patient. In the example of FIG. 1B, IMD 114 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 114 may be coupled to a single lead carrying multiple electrodes or more than two leads each carrying multiple electrodes. IMD 114 may be a chronic electrical stimulator that remains implanted within patient 105 for weeks, months, or even years. In other examples, IMD 114 may be a temporary, or trial, stimulator used to screen or evaluate the efficacy of electrical stimulation for chronic therapy. In one example, IMD 114 is implanted within patient 105, while in another example, IMD 114 is an external device coupled to percutaneously implanted leads.

IMD 114 may be constructed of any polymer, metal, or composite material sufficient to house the components of IMD 114 (e.g., components illustrated in FIG. 2) within patient 105. In this example, IMD 114 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 114 may be implanted within other suitable sites within patient 105, which may depend, for example, on the target site within patient 105 for the delivery of electrical stimulation therapy. The outer housing of IMD 114 may be configured to provide a hermetic seal for components, such as a rechargeable or non-rechargeable power source. In addition, in some examples, the outer housing of IMD 114 is selected from a material that facilitates receiving energy to charge the rechargeable power source.

Electrical stimulation energy, which may be constant current or constant voltage-based pulses, for example, is delivered from IMD 114 to one or more target tissue sites of patient 105 via one or more electrodes (not shown) of implantable leads 130. In the example of FIG. 1B, lead 130A carries electrodes that are placed adjacent to the target tissue of spinal cord 120. In some examples, lead 130B carries electrodes that are placed adjacent to target tissue near a nerve root 125 which leads to a respective peripheral nerves. One or more of the electrodes may be disposed at a distal tip of a lead 130 and/or at other positions at intermediate points along the lead. Leads 130 may be implanted and coupled to IMD 114. The electrodes may transfer electrical stimulation generated by an electrical stimulation generator in IMD 114 to tissue of patient 105. Although leads 130 may each be a single lead, lead 130 may include a lead extension or other segments that may aid in implantation or positioning of lead 130. In some other examples, IMD 114 may be a leadless stimulator with one or more arrays of electrodes arranged on a housing of the stimulator rather than leads that extend from the housing. In addition, in some other examples, system 104 may include one lead or more than two leads, each coupled to IMD 114 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 114 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses are typically predetermined parameter values determined prior to delivery of the stimulation pulses (e.g., set according to a stimulation program). However, in some examples, system 104 changes one or more parameter values automatically based on one or more factors or based on user input.

Although FIG. 1C is directed to a combination of stimulation delivered to the spinal cord and a peripheral nerve, e.g., used to treat pain, in other examples system 104 may be configured to treat any other condition that may benefit from electrical stimulation therapy. For example, system 104 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 104 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105. For example, for PNFS, one of the leads 130 is disposed along the spinal cord 120, and one of the leads is disposed along one or more nerve roots 125, such as one or more nerve roots that extend from spinal cord 120 at respective locations.

In some examples, leads 130 includes one or more sensors configured to allow IMD 114 to monitor one or more parameters of patient 105, such as patient activity, pressure, temperature, or other characteristics. The one or more sensors may be provided in addition to, or in place of, therapy delivery by leads 130.

IMD 114 is configured to deliver electrical stimulation therapy to patient 105 via selected combinations of electrodes carried by one or both of leads 130, alone or in combination with an electrode carried by or defined by an outer housing of IMD 114. The target tissue for the electrical stimulation therapy may be any tissue affected by electrical stimulation, which may be in the form of electrical stimulation pulses or continuous waveforms and may include a first target tissue and a second target tissue. In some examples, the target tissue includes nerves, smooth muscle or skeletal muscle, or peripheral nerves. In the example illustrated by FIG. 1C, a first target tissue is tissue proximate spinal cord 120 or tissue associated with spinal cord 120, such as within an intrathecal space or epidural space of spinal cord 120, or, in some examples, adjacent nerves that branch off spinal cord 120. The second target tissue is one or more nerve roots 125 in this example. In other examples, a first target tissue is a nerve root 125 in the torso or within few or less inches of the spinal cord 120, and the second target tissue may include a tissue near nerve root 125 or associated with a peripheral nerve, such as a more peripheral nerves that extend from a respective nerve root 125. Leads 130 may be introduced into adjacent spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results. For example, as described herein, electrical stimulation may be directed to glial cells while other electrical stimulation (delivered by different electrode combination) is directed to neurons, such as peripheral nerves.

IMD 114 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 114 according to that program. For example, a therapy stimulation program that controls delivery of stimulation by IMD 114 in the form of pulses may define values for voltage or current pulse amplitude, pulse width, and pulse rate (e.g., pulse frequency) for stimulation pulses delivered by IMD 114 according to that program.

A user, such as a clinician or patient 105, may interact with a user interface of an external programmer 150 to program IMD 114. Programming of IMD 114 may refer generally to the generation and transfer of commands, programs, or other information to control the operation of IMD 114. In this manner, IMD 114 may receive the transferred commands and programs from external programmer 150 to control electrical stimulation therapy. For example, external programmer 150 may transmit therapy stimulation programs, stimulation parameter adjustments, therapy stimulation program selections, user input, or other information to control the operation of IMD 114, e.g., by wireless telemetry or wired connection. As described herein, stimulation delivered to the patient may include control pulses, and, in some examples, stimulation may include control pulses and informed pulses.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 114, whereas a patient programmer may support adjustment and selection of such programs by a patient during ordinary use. In other examples, external programmer 150 may include, or be part of, an external charging device that recharges a power source of IMD 114. In this manner, a user may program and charge IMD 114 using one device, or multiple devices.

As described herein, information may be transmitted between external programmer 150 and IMD 114. Therefore, IMD 114 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 114 implant site to improve the quality or security of communication between IMD 114 and external programmer 150. Communication between external programmer 150 and IMD 114 may occur during power transmission or separate from power transmission.

In some examples, IMD 114, in response to commands from external programmer 150, delivers electrical stimulation therapy according to a plurality of therapy stimulation programs to a target tissue site of the spinal cord 120 of patient 105 via electrodes (not depicted) on leads 130, and to a target tissue site of nerve root 125. In some examples, IMD 114 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Optionally, pain relief may also be used by position the leads in the neighborhood of nerve root 125 in addition to positioning one of the leads near the spinal cord 120. Peripheral Nerve Stimulation (PNS) is an alternative therapy for chronic pain in which a target nerve has been identified to be the source of pain. The current understanding of the therapeutic effects of PNS is also based on the gate control theory. However, axons of sensory neurons in peripheral nerves are surrounded by glial cells that are known to respond accordingly to the frequency characteristics of a stimulus.

Figure 2:
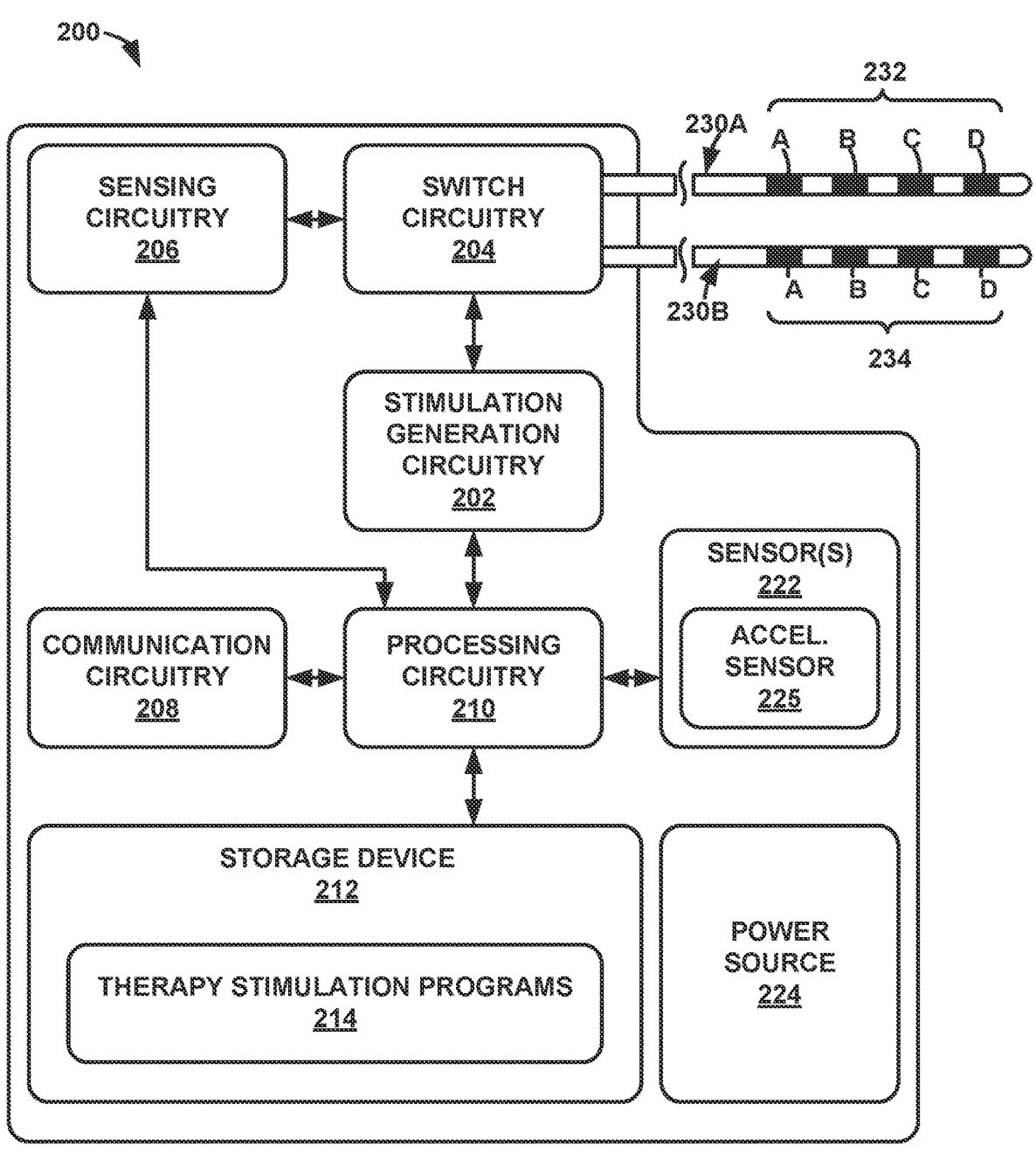
FIG. 2 is a block diagram illustrating an example configuration of components of an IMD, in accordance with one or more techniques of this disclosure.

FIG. 2 is a block diagram illustrating an example configuration of components of IMD 200, in accordance with one or more techniques of this disclosure. IMD 200 may be an example of IMD 110A, B of FIG. 1A, or IMD 112 of FIG. 1B. In the example shown in FIG. 2, IMD 200 includes stimulation generation circuitry 202, switch circuitry 204, sensing circuitry 206, communication circuitry 208, processing circuitry 210, storage device 212, sensor(s) 222, and power source 224.

In the example shown in FIG. 2, storage device 212 stores therapy stimulation programs 214 within storage device 212. Each stored therapy stimulation program of therapy stimulation programs 214 defines values for a set of electrical stimulation parameters (e.g., a stimulation parameter set for each pulse train or each slot of a series of slots), such as a stimulation electrode combination, electrode polarity, current or voltage amplitude, pulse width, pulse rate, and pulse shape.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as evoked compound action potentials (ECAPs). In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Communication circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via communication circuitry 208. Updates to the therapy stimulation programs 214 may be stored within storage device 212. Communication circuitry 208 in IMD 200, as well as telemetry circuits in other devices and systems described herein, such as the external programmer, may accomplish communication by radiofrequency (RF) communication techniques. In addition, communication circuitry 208 may communicate with an external medical device programmer (not shown in FIG. 2) via proximal inductive interaction of IMD 200 with the external programmer. The external programmer may be one example of external programmer 150 of FIG. 1A or 1B. Accordingly, communication circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to therapy stimulation programs 214 and ECAP test stimulation programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234.

In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient or signals near a peripheral nerve (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques.

Storage device 212 may be configured to store information within IMD 200 during operation. Storage device 212 may include a computer-readable storage medium or computer-readable storage device. Storage device 212 may include, for example, random access memories (RAM), dynamic random access memories (DRAM), static random access memories (SRAM), ferroelectric random access memories (FRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store therapy stimulation programs 214.

Sensor(s) 222 may include one or more sensing elements that sense values of a respective patient parameter. As described, electrodes 232 and 234 may be the electrodes that sense the characteristic value of the ECAP. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. IMD 200 may include additional sensors within the housing of IMD 200 and/or coupled via one of leads 130 or other leads. In addition, IMD 200 may receive sensor signals wirelessly from remote sensors via communication circuitry 208, for example. In some examples, one or more of these remote sensors may be external to patient (e.g., carried on the external surface of the skin, attached to clothing, or otherwise positioned external to patient 105).

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. In other examples, power source 224 may include one or more primary batteries that are not rechargeable. Power source 224 may include any one or more of a plurality of different battery types, such as nickel cadmium batteries and lithium ion batteries.

Figure 3:
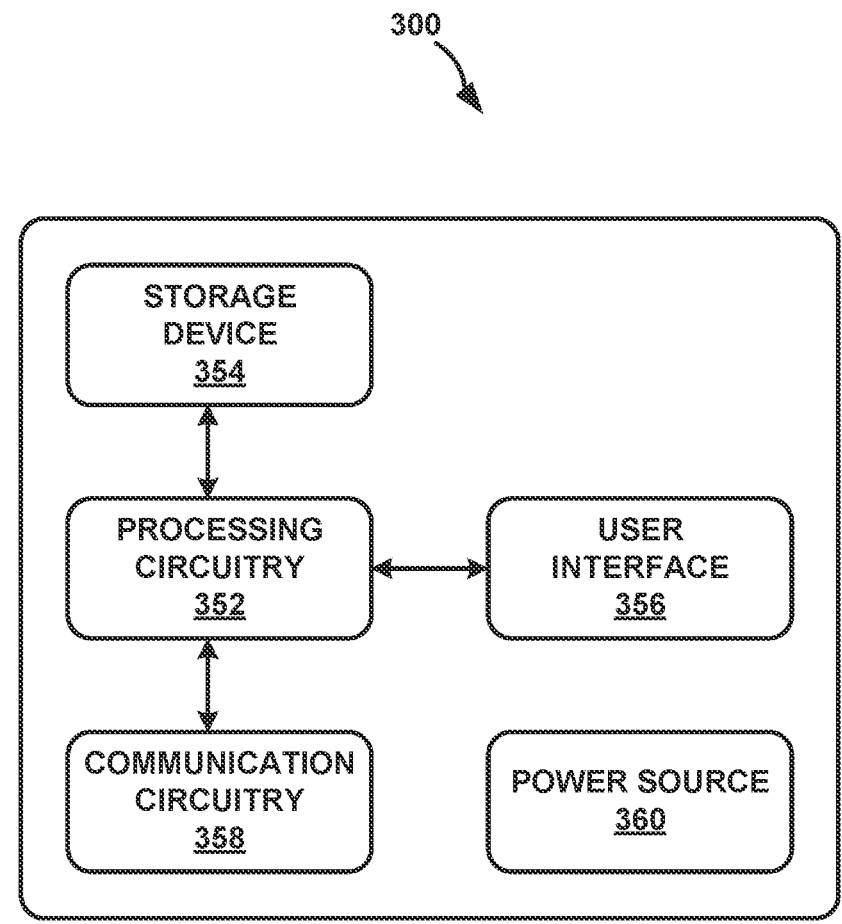
FIG. 3 is a block diagram illustrating an example configuration of components of an external programmer, in accordance with one or more techniques of this disclosure.

FIG. 3 is a block diagram illustrating an example configuration of components of external programmer 300, in accordance with one or more techniques of this disclosure. External programmer 300 may be an example of external programmer 150 of FIG. 1A or 1B. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, communication circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and communication circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and communication circuitry 358 are described as separate modules, in some examples, processing circuitry 352 and communication circuitry 358 are functionally integrated. In some examples, processing circuitry 352 and communication circuitry 358 correspond to individual hardware units, such as ASICs. DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines stimulation pulses, such as control pulses and/or informed pulses. Storage device 354 may also store data received from a medical device (e.g., IMD 110). For example, storage device 354 may store ECAP related data recorded at a sensing module of the medical device, and storage device 354 may also store data from one or more sensors of the medical device. This ECAP related data may include ECAP information transmitted from an implantable medical device, such as IMD 110.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. In addition, as described herein, processing circuitry 352 may control user interface 356 to present graphical representations of ECAP information transmitted by IMD 110. User interface 356 may also receive user input via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Communication circuitry 358 may support wireless communication between the medical device and external programmer 300 under the control of processing circuitry 352. Communication circuitry 358 may also be configured to communicate with another computing device via wireless communication techniques, or direct communication through a wired connection. In some examples, communication circuitry 358 provides wireless communication via an RF or proximal inductive medium. In some examples, communication circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, communication circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1A, 1B). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
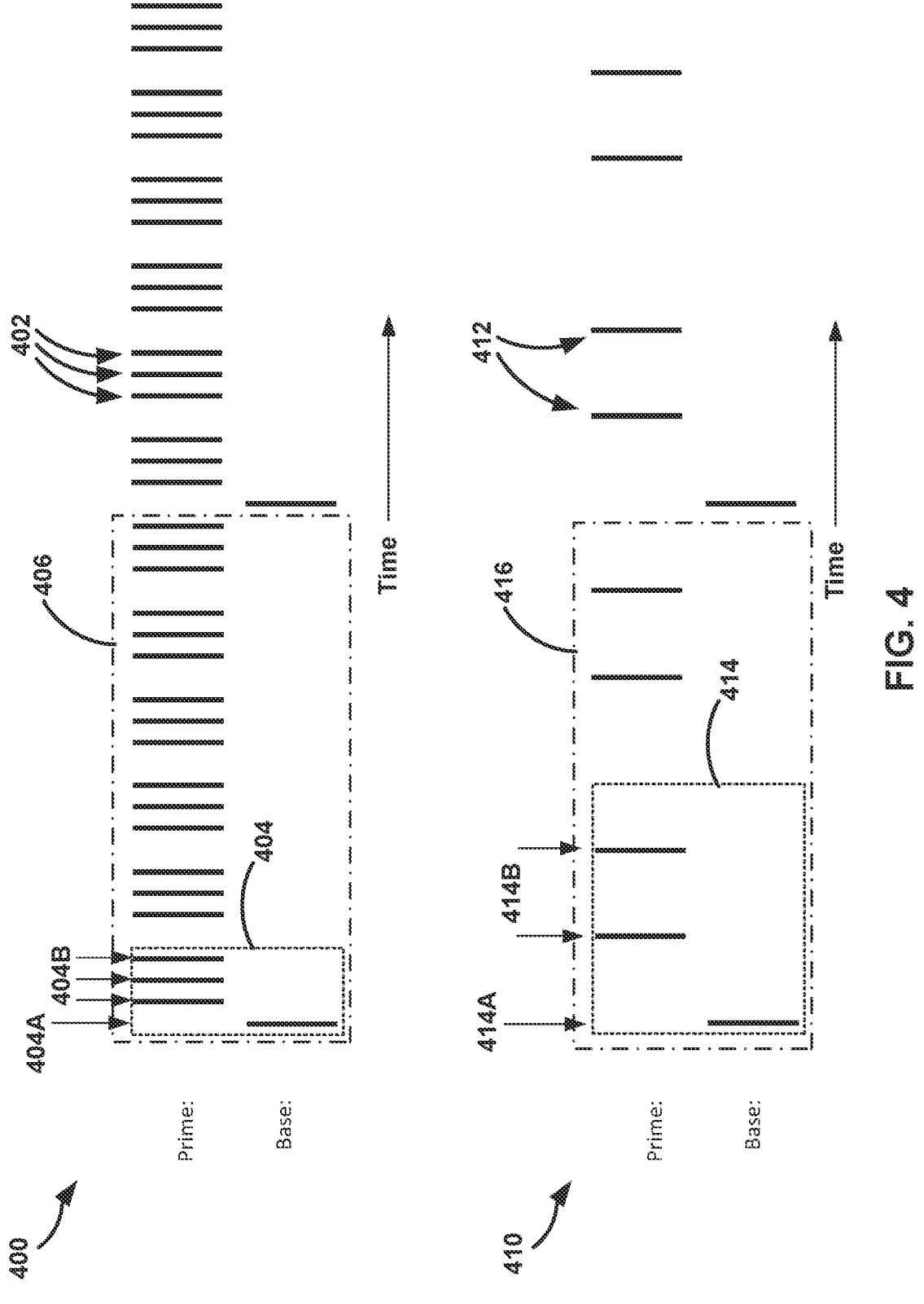
FIG. 4 is a timing diagram illustrating an example of electrical stimulation pulses delivered according to different stimulation patterns.

FIG. 4 is a timing diagram illustrating an example of electrical stimulation pulses delivered according to different stimulation patterns. As shown in FIG. 4, timing diagrams 400 and 410 provide examples of different methods for delivering multimodal stimulation. Timing diagram 400 shows that pulses 402 can be delivered to two different target tissues, such as the prime pulses in the upper train being delivered to glial cells (e.g., glial cells on the spinal cord or glial cells at or near the peripheral nerve), as one example. Pulses 402 in the lower train are less frequent and delivered to a different target tissue, such as neurons associated with the peripheral nerve. Series of slots 404 (e.g., slot 404A and slots 404B) indicates that there are four slots that represent a period of time during which a single stimulation pulse can be delivered. Put another way, 4 programs (or respective pulse trains) can be active at the same time, which one pulse from each program being deliverable in its respective slot. The series of slots 404 then continues to repeat over time. In this manner, the pulses of the four programs (or respective pulse trains) are at least partially interleaved over time.

In the upper train example, the prime stimulation includes pulses delivered during the second, third, and fourth slots 404B of each series of slots 404. The group rate determines the frequency that the series of slots 404 is repeated. Therefore, if the group rate is 300 Hz, the pulses of the upper train have a maximum interpulse frequency of 1200 Hz and an average of 900 Hz is achieved because the first slot of every series of slots 404 is occupied by the lower train program (the base stimulation) delivered to a different target tissue via a different electrode combination. As shown in the lower train of timing diagram 400, the pulse in slot 404A is only delivered once every sixth occurrence of series of slots 404. When the pulse is not delivered in a series of slots 404, that slot remains empty such that no pulse is delivered. Therefore, the lower train achieves a frequency of 50 Hz. Pattern 406 indicates one complete repeating pattern for the upper and lower trains together. As IMD 200 continues to deliver pulses according to the programs and repeating series of slots 404, stimulation is delivered repeatedly with pattern 406 as long as stimulation is being delivered.

However, timing diagram 410 indicates stimulation delivery that consumes more power than may be necessary to treat the patient. Instead, the prime stimulation (e.g., the upper train delivered to glial cells) may be effective at much lower average pulse frequencies. This lower average frequency is still greater than the base frequency of the lower pulse train, but it may enable IMD 200 to conserve power proportional the fewer number of pulses generated by IMD 200 than in timing diagram 300. In the example of timing diagram 410, the first stimulation may include one or more trains of electrical stimulation pulses 412 in the upper train labeled as "prime" pulses. The second stimulation may include a train of electrical stimulation pulses 412 in the lower train labeled "base" pulses. Since series of slots 414 (e.g., slots 414A and 414B) only includes three slots, three pulses are shown in respective slots in time. The series of slots 414 has a group rate of 100 Hz, and the second stimulation only includes a pulse in the first slot 414A of every other series of pulses 414 such that the second stimulation has a frequency of 50 Hz. The first stimulation of the upper train includes two trains of pulses (but could include three or more distinct trains), where one train includes a pulse in the second slot of slots 414B of every series of pulses 414 and another train includes a pulse in the third slot of slots 414B of every series of pulses 414. In this manner, each train in the upper train has a respective frequency of 100 Hz, which results in an interpulse frequency of 300 Hz for the upper train and an average frequency of 200 Hz. Pattern 416 indicates one complete repeating pattern for the upper and lower trains together. As IMD 200 continues to deliver pulses according to the programs and repeating series of slots 414, stimulation is delivered repeatedly with pattern 416 as long as stimulation is being delivered. Generally, each frequency of the respective pulse trains in the upper train are greater than the frequency of the lower pulse train.

Although the concept of a series of slots is provided as one example mechanism for managing the delivery of pulses for the first and second stimulation pulses, other management techniques may be used in other examples. For example, IMD 200 may have a flexible programming architecture that enables processing circuitry 210 to schedule different pulses for different electrode combinations at any frequency desired. For example, IMD 200 may simply run multiple different programs that define respective pulse trains interleaved as needed to achieve the respective frequencies of each pulse train.

Figure 5:
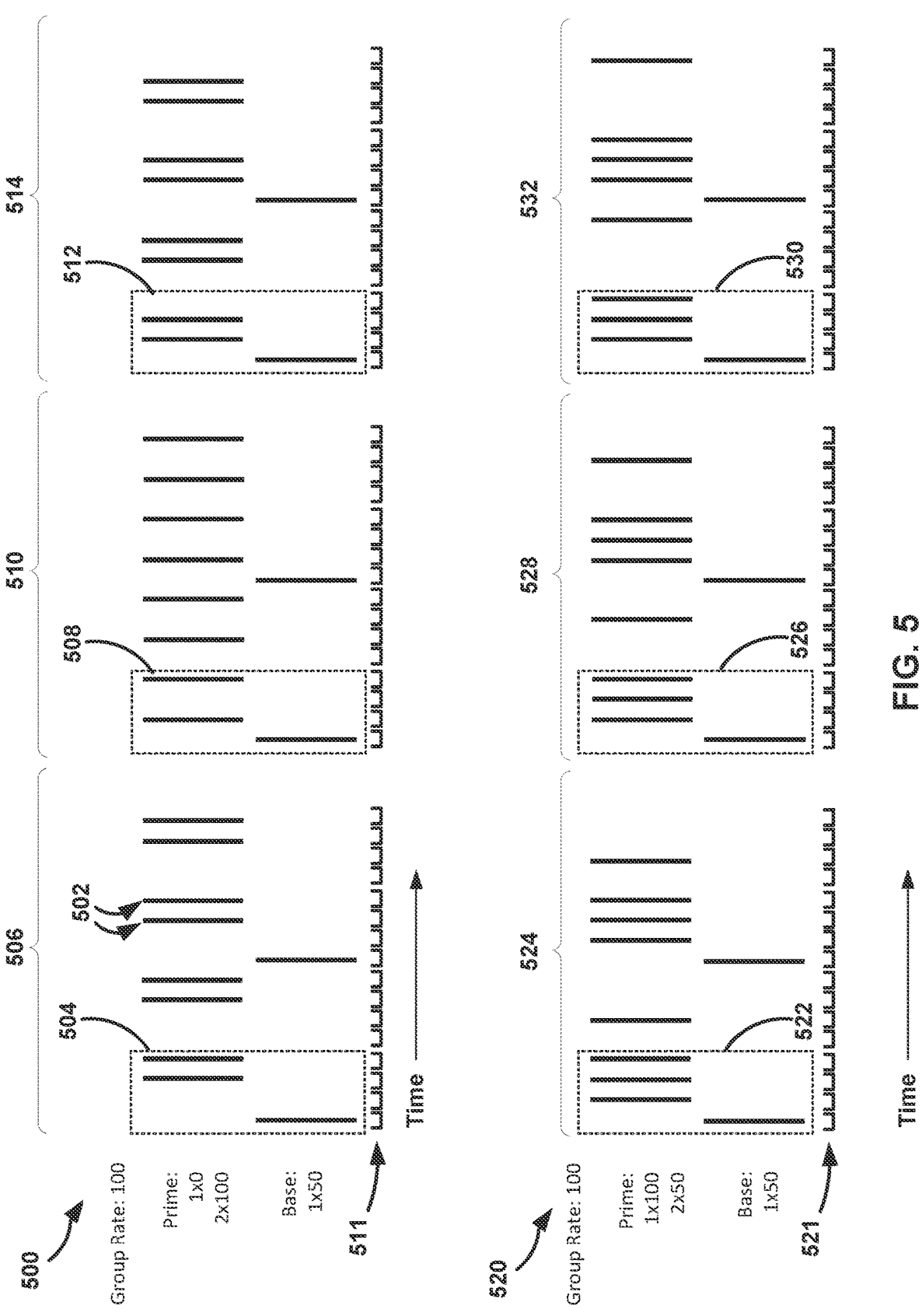
FIG. 5 is a timing diagram illustrating an example of electrical stimulation pulses delivered according to different stimulation patterns.

FIG. 5 includes timing diagrams 500 and 520 illustrating an example of electrical stimulation pulses delivered according to different stimulation patterns. Timing diagrams 500 and 520 may be similar to timing diagram 410 of FIG. 4 because they are set to provide low energy stimulation as compared to higher frequency prime stimulation. As shown in timing diagram 500, different patterns 506, 510, and 514 are possible with different pulses 502 with a group rate of 100 Hz for series of slots that includes 4 slots. In pattern 506, series of slots 504 has four slots where the first slot includes a pulses for the base stimulation to achieve 50 Hz stimulation, the second slot is left empty, and the third and fourth slots include respective 100 Hz pulse trains for the prime stimulation. Therefore, the resulting prime stimulation is delivered with an average of 200 Hz and an interpulse frequency of 400 Hz. In pattern 510, series of slots 508 has four slots where the first slot includes a pulses for the base stimulation to achieve 50 Hz stimulation, the third slot is left empty, and the second and fourth slots include respective 100 Hz pulse trains for the prime stimulation. Therefore, the resulting prime stimulation is delivered with an average of 200 Hz and an interpulse frequency of 200 Hz. In pattern 514, series of slots 512 has four slots where the first slot includes a pulses for the base stimulation to achieve 50 Hz stimulation, the fourth slot is left empty, and the second and third slots include respective 100 Hz pulse trains for the prime stimulation. Therefore, the resulting prime stimulation is delivered with an average of 200 Hz and an interpulse frequency of 400 Hz.

As shown in timing diagram 520, different patterns 524, 528, and 532 are possible with a group rate of 100 Hz for series of slots that includes 4 slots. In pattern 524, series of slots 522 has four slots where the first slot includes a pulses for the base stimulation to achieve 50 Hz stimulation, the second slot includes pulses for a 100 Hz pulse train, and the third and fourth slots include pulses for respective 50 Hz pulse trains for the prime stimulation. Therefore, the resulting prime stimulation is delivered with an average of 200 Hz and an interpulse frequency of 400 Hz for three consecutive pulses. In pattern 528, series of slots 526 has four slots where the first slot includes a pulses for the base stimulation to achieve 50 Hz stimulation, the third slot includes pulses for a 100 Hz pulse train, and the second and fourth slots include pulses for respective 50 Hz pulse trains for the prime stimulation. Therefore, the resulting prime stimulation is delivered with an average of 200 Hz and an interpulse frequency of 400 Hz for three consecutive pulses. In pattern 532, series of slots 530 has four slots where the first slot includes a pulses for the base stimulation to achieve 50 Hz stimulation, the fourth slot includes pulses for a 100 Hz pulse train, and the second and third slots include pulses for respective 50 Hz pulse trains for the prime stimulation. Therefore, the resulting prime stimulation is delivered with an average of 200 Hz and an interpulse frequency of 400 Hz for three consecutive pulses. Although a group rate of 100 is described, the group rate may be adjusted according to the number of slots in the series of slots and the desired frequencies to achieve for each type of stimulation.

In some examples, it may be desirable for the pulses in the prime stimulation pulse train to be less than uniform, approaching random, or completely random. For this reason, pattern 532 may be used to achieve a more random pattern of pulses. In other examples, IMD 200 may alternative between two or more of the patterns of FIG. 5, or other patterns, in order to further change the pattern that is repeated during stimulation delivery for the prime stimulation.

Figure 6:
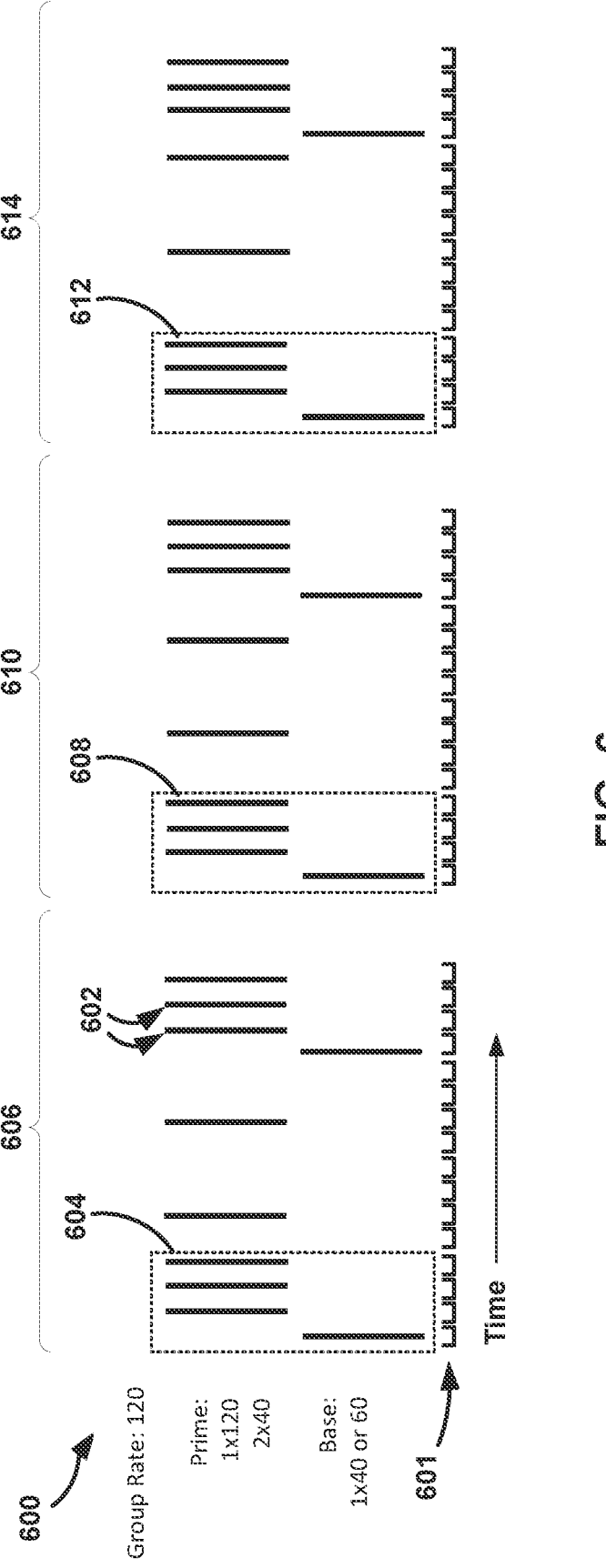
FIG. 6 is a timing diagram illustrating an example of electrical stimulation pulses delivered according to different stimulation patterns.

FIG. 6 is a timing diagram illustrating an example of electrical stimulation pulses delivered according to different stimulation patterns. Timing diagram 600 may be similar to timing diagrams of FIGS. 4 and 5 because they are set to provide low energy stimulation as compared to higher frequency prime stimulation. However, timing diagram has a group rate of 120 Hz, which is slightly higher than the group rates of the series of slots of FIG. 5. As shown in timing diagram 600, different patterns 606, 610, and 614 are possible with a group rate of 120 Hz for series of slots that includes 4 slots within which pulses 602 can be delivered. In pattern 606, series of slots 604 has four slots where the first slot includes a pulses for the base stimulation to achieve 40 Hz stimulation, the second slot includes pulses for a 120 Hz pulse train, and the third and fourth slots include pulses for respective 40 Hz pulse trains for the prime stimulation. Therefore, the resulting prime stimulation is delivered with an average of 240 Hz and an interpulse frequency of 480 Hz for three consecutive pulses. In pattern 610, series of slots 608 has four slots where the first slot includes a pulses for the base stimulation to achieve 40 Hz stimulation, the third slot includes pulses for a 120 Hz pulse train, and the second and fourth slots include pulses for respective 40 Hz pulse trains for the prime stimulation. Therefore, the resulting prime stimulation is delivered with an average of 240 Hz and an interpulse frequency of 480 Hz for three consecutive pulses. In pattern 614, series of slots 612 has four slots where the first slot includes a pulses for the base stimulation to achieve 40 Hz stimulation, the fourth slot includes pulses for a 120 Hz pulse train, and the second and third slots include pulses for respective 40 Hz pulse trains for the prime stimulation. Therefore, the resulting prime stimulation is delivered with an average of 240 Hz and an interpulse frequency of 480 Hz for three consecutive pulses. Although a group rate of 120 is described, the group rate may be adjusted according to the number of slots in the series of slots and the desired frequencies to achieve for each type of stimulation. In other examples, the base stimulation may have a frequency of approximately 60 Hz. For any of the examples of herein, IMD 200 may switch the prime stimulation from one target tissue to another target tissue in order to achieve efficacious therapy.

In some examples, IMD 200 may change the order of pulses of one train of electrical stimulation pulses in the prime train with pulses of another train of electrical stimulation pulses over time to adjust a pulse pattern created by interleaving the at least of the electrical stimulation pulses of the trains of electrical stimulation pulses used to generate the overall prime train of stimulation pulses.

In some examples, the average frequency of the prime stimulation is selected from a frequency range from approximately 900 Hz to approximately 1200 Hz. In some examples, the average frequency of the prime stimulation is at least 130 Hz. In some examples, the average frequency of the prime stimulation is selected from a frequency range from approximately 130 Hz to approximately 400 Hz. In some examples, the average frequency of the prime stimulation is selected from a frequency range from approximately 130 Hz to approximately 600 Hz. In some examples, the average frequency of the prime stimulation is selected from a frequency range from approximately 130 Hz to approximately 1200 Hz. In some examples, the average frequency of the prime stimulation is selected from a frequency range from approximately 130 Hz to approximately 1400 Hz. In some examples, the average frequency of the base stimulation is selected from a frequency range from approximately 10 Hz to approximately 60 Hz. In some examples, the average frequency of the base stimulation is selected from a frequency range from approximately 40 Hz to approximately 60 Hz. In some examples, the frequency of the base stimulation may be lower than 130 Hz. In some examples, the base stimulation frequency may be lower than the prime frequency. In some examples, IMD 200 may include the amplitude of base stimulation until the patient achieves effective pain relief.

In some examples, IMD 200 may cycle between a first mode of a first period of time and a second mode of a second period of time, wherein the first mode comprises generating the first train of electrical stimulation pulses (e.g., the prime stimulation) at least partially interleaved with the second train of electrical stimulation pulses (e.g., the base stimulation). The second mode may include withholding generation of the first train of electrical stimulation pulses and the second train of electrical stimulation pulses. In some examples, the ratio of the first period to the second period of time is between approximately 1:1 and 1:3. In other examples, the ratio may be lower to enable much longer off periods for stimulation. In one example, the first period of time for stimulation is selected from a range from approximately 1 minute to approximately 30 minutes. In another example, the first period of time for stimulation is selected from a range from approximately 5 minute to approximately 15 minutes. In some examples, the on period for stimulation may be less than 1 minute or greater than 30 minutes.

In some examples, IMD 200 may cycle between a first mode of a first period of time and a second mode of a second period of time, wherein the first mode comprises generating the first train of electrical stimulation pulses (e.g., the prime stimulation) at least partially interleaved with the second train of electrical stimulation pulses (e.g., the base stimulation), and the first period of time may be staggered from the second period of time. In some examples, the first period of time may be precisely staggered, or may be randomly staggered. In some examples, the first train of pulses may occur at the same time as the second train of pulses, i.e., they are not staggered.

In some examples, the amplitude of pulses of the first train of electrical stimulation pulses (e.g., the prime stimulation) is below at least one of a perception threshold or a sensory threshold of a patient. In some examples, the amplitude of pulses of the second train of electrical stimulation pulses (e.g., the base stimulation) is below at least one of a perception threshold or a sensory threshold of a patient. In some examples, the stimulation pulses are delivered at 60% of threshold.

The amplitude of a priming component may be set at a value below a Priming Perception Threshold (PPT), although setting it at or above the PPT is not excluded. The PPT may be found by slowly increasing the amplitude while feedback is obtained from the subject. Once the onset of perception is recorded, then the amplitude of the priming component may be changed to a value which is a percentage of the PPT (% PPT). With an exemplary PF of 200 Hz, the signal may be then set for a given time, e.g., 10-30 minutes, before an electric component set at a tonic frequency lower than the PF, e.g., 10 Hz to 199 kHz, is applied independently to other electrodes in the lead. In the prime mode of stimulation, the tonic frequency will be lower than the priming frequency but is not necessarily limited to a particular range of frequencies below the priming frequency.

The Pulse Width (PW) of a charge-balanced, e.g., a biphasic symmetric, biphasic asymmetric, or capacitor coupled monophasic, pulsed signal can be as low as 10 μs and as large as allowed by the set tonic frequency. In exemplary embodiments, the pulse width may be between about 100 and 500 microseconds, between about 100 and 400 microseconds, between about 150 and 200 microseconds, or any different value, range or combinations of pulse widths. In one example, the PW may be approximately 170 microseconds or 200 microseconds. The PW of pulses of prime stimulation may be the same or different than the PW of base stimulation.

The signal generation and delivery circuitry may also allow for modifying the duty cycles of pulsed width signals and various schemes in which the time of initial priming can be varied, as well as the times in which the priming signal is on or off relative to the time when the tonic signal is delivered. The amplitude of the tonic electrical component, which could be either voltage or current controlled, may be set above, below or at the Tonic Perception Threshold (TPT). PT may be obtained by increasing the amplitude of the tonic component while getting feedback from the patient. The tonic amplitude may then be set to a value corresponding to a percentage of the TPT (% TPT). In the prime multimodal modulation methods described herein both the priming component and the tonic component may be below 100 kHz, in one embodiment. In another embodiment, the tonic signal may be below 500 Hz. In still another embodiment, the tonic signal may be below 100 Hz. In one embodiment, the ratio of priming component frequency to tonic component frequency may be in the range of 2:1 to 40:1, 4:1 to 40:1, 10:1 to 40:1, 20:1 to 40:1, up to 70:1, up to 140:1, etc. depending on the specific values of the frequencies chosen.

In yet another embodiment of a method of delivering therapy, the priming component may be biphasic in which the polarity of the first phase of the biphasic prime component may be either cathodic or anodic. With this embodiment, the tonic component may have characteristics that are different from those of the priming component. The tonic component may be biphasic with the polarity of the first phase of the biphasic tonic signal being either cathodic or anodic.

In exemplary embodiments of multimodal modulation therapy, an active recharge mode provides a recovery pulse that applies an equal charge in a direction opposite to the input, thus driving the waveform each way.

In one or more examples, the timing of delivering base and prime pulses may be coordinated relative to the delivery of the base pulses and the prime pulses. For example, the base pulses may be delivered at a first tissue location at a first time, the prime pulses may be delivered at a second time at a second tissue location that is remote or different than the first tissue location, where the first time of delivery may be different than the second time of delivery. The timing of the base and prime pulses may be controlled relative to each other to account for the distance between the first tissue location and the second tissue location. In some examples, the timing of the base and prime pulses may be determined based on nerve propagation speeds between the first tissue location and the second tissue location.

Figure 7:
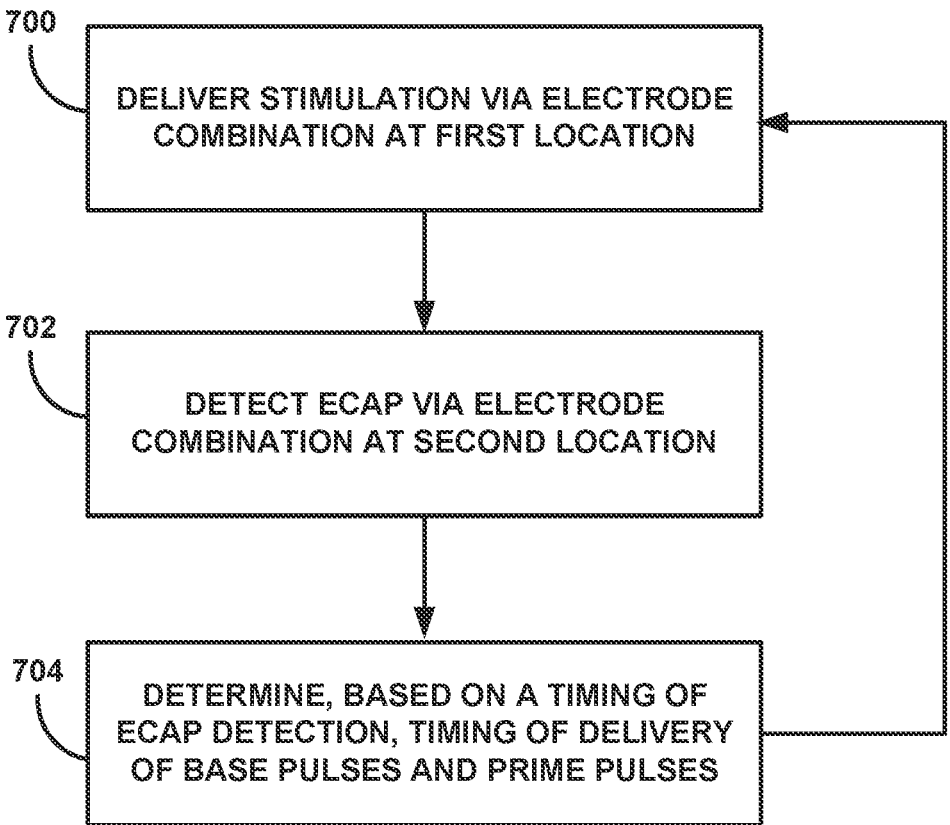
FIG. 7 is a flow diagram illustrating an example technique for delivering electrical stimulation according to a specific pattern of pulses having different pulse frequencies.

FIG. 7 is a flow diagram illustrating an example technique for delivering electrical stimulation. For convenience, FIG. 7 is described with respect to IMD 200 of FIG. 2. However, the techniques of FIG. 7 may be performed by different components of IMD 200 or by additional or alternative medical devices, such as programmer 300.

In the example of FIG. 7, processing circuitry 210 delivers stimulation to a first location via a first electrode combination (700). For example, stimulation may be provided at the first tissue location via electrodes carried by a first lead. In some examples, the system may sense an ECAP at the second tissue location via a second electrode combination different than the first electrode combination, such as with electrodes carried by a second lead different than the first lead (702). In some examples, the ECAP may be sensed with electrodes of the second lead at a peripheral nerve of a patient. In other words, the first electrode combination can deliver an electrical stimulus that elicits an ECAP that is detected by a second electrode combination. The first tissue location may be the spinal cord and the second tissue location may be a peripheral nerve or dorsal root, or vice versa. In some examples, the system only performs the steps 700 and 702 while the patient is still in order to reduce electrical noise generated by moving muscles or other patient activity. In this manner, processing circuitry 210 may only perform steps 700 and 702 in response to determining that the activity level (e.g., movement or muscle activity of the patient) is below a predetermined threshold.

The timing of the sensed ECAP, for example the time difference between delivery of the stimulation at the first tissue location and the sensing of ECAP at the second tissue location, may be used by processing circuitry 210 to determine the timing of the base pulses and the prime pulses (704). In one or more examples, this timing may indicate the time delay between signal propagation between the two tissue locations. Processing circuitry 210 may know the rate of the first stimulation (e.g., a base pulse) and timing of the second stimulation (e.g., a prime pulse) based on when the ECAP signals are detected. In this manner, the system may incorporate the time delay into scheduling the timing of delivery of the base pulses relative to the prime pulses. Since the prime pulses may affect the neurological response to the base pulses, and vice versa, the system may include this time delay in order for the prime pulses and base pulses to provide effective therapy to the patient. In some examples, processing circuitry 210 may adjust the timing of delivery between the base pulses and the prime pulses to generate a constructive therapeutic effect by timing the base pulses and the prime pulses to arrive at tissue at the same time and/or in phase. In other examples, processing circuitry 210 may adjust the timing of delivery between the base pulses and the prime pulses to generate an interfering therapeutic effect by timing the base pulses and the prime pulses to arrive at tissue at a different time and partially or fully out of phase.

In some examples, the system can adjust the timing of delivery between the base pulses and prime pulses until the sensed ECAP signal indicates the base and/or priming pulses provide effective therapy (e.g., a sensed ECAP going below a threshold indicative of pain reduction or a sensed ECAP achieving a target ECAP level indicative of acceptable pain management, such as paresthesia. In some examples, one or more stimulation parameters may be adjusted at the first electrode combination until a resulting detectable ECAP at the second lead may be sensed. In some examples, the system may adjust one or more stimulation parameters, such as one or more of current or voltage amplitude, pulse width, electrode combination, pulse frequency, etc.

In some examples, the sensed ECAP may be used to identify specific nerve fibers desired for stimulation. For example, painful nerve fibers are typically nonmyelinated and go slower as opposed to faster nerve fibers. Therefore, the system may determine the timing between the base pulses and prime pulses in order to affect the slower nerve fibers and/or select other stimulation parameters to target the slower nerve fibers as indicated by the sensed ECAP signal.

Figure 8:
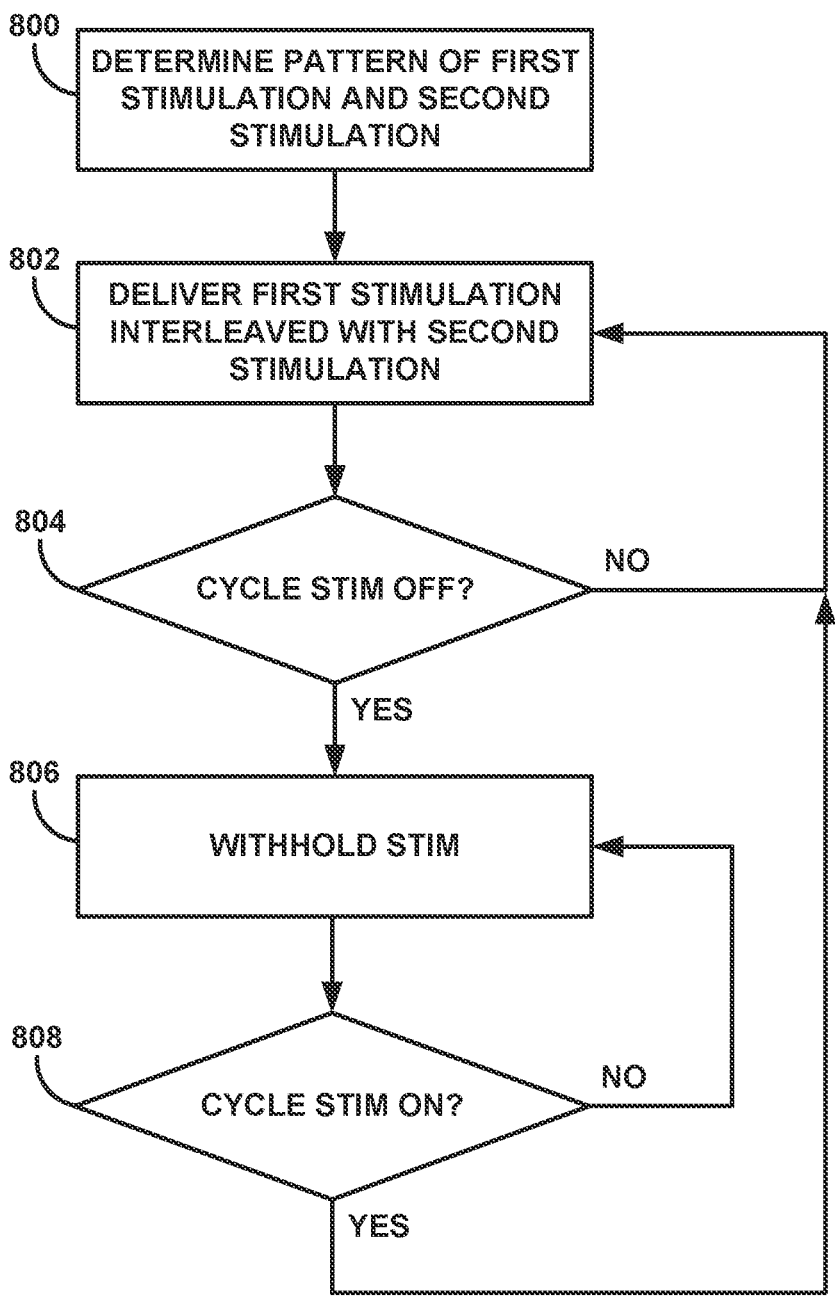
FIG. 8 is a flow diagram illustrating an example technique for delivering electrical stimulation according to a specific pattern of pulses having different pulse frequencies.

FIG. 8 is a flow diagram illustrating an example technique for delivering electrical stimulation according to a specific pattern of pulses having different pulse frequencies. For convenience, FIG. 8 is described with respect to IMD 200 of FIG. 2. However, the techniques of FIG. 8 may be performed by different components of IMD 200 or by additional or alternative medical devices, such as programmer 300.

In the example of FIG. 8, processing circuitry 210 determines the pattern of the first and second stimulation to be delivered to the patient (800). This pattern may include determining which slots of a series of slots includes respective pulses for prime stimulation and base stimulation or otherwise determining the manner in which pulses of a first stimulation delivered to a first target tissue (e.g., glial cells) will be interleaved with pulses of a second stimulation delivered to a second target tissue (e.g., peripheral nerve). Processing circuitry 210 then delivers the first stimulation interleaved with the second stimulation (802) until cycling instructions indicate to turn off stimulation (804). If instructions indicate that the time period for stimulation has not elapsed ("NO" branch of block 804), processing circuitry 210 continues to deliver stimulation. If instructions indicate that the time period for stimulation has elapsed ("YES" branch of block 804), processing circuitry 210 withholds or ceases stimulation delivery (806). In response to the time period of no stimulation elapsing ("YES" branch of block 808), processing circuitry 210 again delivers stimulation (802).

The following examples are described herein.

Example 1. A method comprising: generating, by stimulation generation circuitry, a first train of electrical stimulation pulses at a first frequency to a first target tissue; and generating, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, wherein at least the first target tissue is associated with a spinal cord of a patient, and the second target tissue comprises at least one of a peripheral nerve or a nerve root of the patient.

Example 2. The method of example 1, wherein the first frequency for the first train of pulses is selected from a frequency range from approximately 900 Hz to approximately 1200 Hz.

Example 3. The method of example 1, wherein the first frequency for the first train of pulses is selected from a frequency range from approximately 130 Hz to approximately 600 Hz.

Example 4. The method of any of examples 1 through 3, wherein the second frequency for the second train of pulses is selected from a frequency range from approximately 10 Hz to approximately 60 Hz.

Example 5. The method of any of examples 1 through 4, wherein the first train of electrical stimulation pulses is subthreshold.

Example 6. The method of any of examples 1 through 5, wherein the second train of electrical stimulation pulses is subthreshold.

Example 7. The method of any of examples 1 through 6, wherein the first target tissue comprises glial cells, and wherein the second target tissue comprises neurons.

Example 8. The method of any of examples 1 through 6, wherein the first target tissue comprises a peripheral nerve root.

Example 9. A method comprising: generating, by stimulation generation circuitry, a first train of electrical stimulation pulses at a first frequency to a first target tissue; and generating, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses; wherein at least the first target tissue is associated with at least one of a peripheral nerve or nerve root of a patient, and the second target tissue is associated with a spinal cord of the patient.

Example 10. The method of example 9, wherein the first frequency for the first train of pulses is selected from a frequency range from approximately 900 Hz to approximately 1200 Hz.

Example 11. The method of example 9, wherein the first frequency for the first train of pulses is selected from a frequency range from approximately 130 Hz to approximately 600 Hz.

Example 12. The method of any of examples 9 through 11, wherein the second frequency for the second train of pulses is selected from a frequency range from approximately 10 Hz to approximately 60 Hz.

Example 13. The method of any of examples 9 through 12, wherein the first train of electrical stimulation pulses is subthreshold.

Example 14. The method of any of examples 9 through 13, wherein the second train of electrical stimulation pulses is subthreshold.

Example 15. The method of any of examples 9 through 14, wherein the first target tissue comprises glial cells, and wherein the second target tissue comprises neurons.

Example 16. The method of any of examples 9 through 15, wherein the first target tissue comprises a peripheral nerve root.

Example 17. A medical device comprising: processing circuitry configured to control stimulation generation circuitry to: generate a first train of electrical stimulation pulses at a first frequency to a first target tissue; and generate a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, wherein at least the first target tissue is associated with a spinal cord of a patient, and wherein the second target tissue is associated with at least one of a peripheral nerve or a nerve root of the patient.

Example 18. The medical device of example 17, wherein the first frequency for the first train of pulses is selected from a frequency range from approximately 900 Hz to approximately 1200 Hz.

Example 19. The medical device of example 17, wherein the first frequency for the first train of pulses is selected from a frequency range from approximately 130 Hz to approximately 600 Hz.

Example 20. The medical device of any of examples 17 through 19, wherein the second frequency for the second train of pulses is selected from a frequency range from approximately 10 Hz to approximately 60 Hz.

Example 21. The medical device of any of examples 17 through 20, wherein the first train of electrical stimulation pulses is subthreshold.

Example 22. The medical device of any of examples 17 through 21, wherein the second train of electrical stimulation pulses is subthreshold.

Example 23. The medical device of any of examples 17 through 22, wherein the first target tissue comprises glial cells, and wherein the second target tissue comprises neurons.

Example 24. The medical device of any of examples 17 through 23, wherein the first target tissue comprises a peripheral nerve root.

Example 25. The medical device of any of examples 17 through 24, further comprising the stimulation generation circuitry.

Example 26. The medical device of any of examples 17 through 25, wherein the second target tissue is associated with a spinal cord of the patient.

Example 27. A medical device comprising: processing circuitry configured to control stimulation generation circuitry to: generate a first train of electrical stimulation pulses at a first frequency to a first target tissue; and generate a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, and wherein at least the first target tissue is associated with at least one of a peripheral nerve or a nerve root of a patient, and the second target tissue is associated with a spinal cord of the patient.

Example 28. The medical device of example 27, wherein the first frequency for the first train of pulses is selected from a frequency range from approximately 900 Hz to approximately 1200 Hz.

Example 29. The medical device of example 27, wherein the first frequency for the first train of pulses is selected from a frequency range from approximately 130 Hz to approximately 600 Hz.

Example 30. The medical device of any of examples 27 through 29, wherein the second frequency for the second train of pulses is selected from a frequency range from approximately 10 Hz to approximately 60 Hz.

Example 31. The medical device of any of examples 27 through 30, wherein the first train of electrical stimulation pulses is subthreshold.

Example 32. The medical device of any of examples 27 through 31, wherein the second train of electrical stimulation pulses is subthreshold.

Example 33. A computer-readable storage medium comprising instructions that, when executed, cause processing circuitry to: control stimulation generation circuitry to generate a first train of electrical stimulation pulses at a first frequency to a first target tissue; and control the stimulation generation circuitry to generate a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, wherein at least the first target tissue is associated with a spinal cord of a patient, and the second target tissue is associated with at least one of a peripheral nerve or a nerve root of the patient.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), ferroelectric random access memory (FRAM), DRAM, SRAM, FRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical device comprising:
   processing circuitry configured to:
      control stimulation generation circuitry to:
         generate a first train of electrical stimulation pulses at a first frequency to a first target tissue; and
         generate a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, wherein at least the first target tissue is associated with one of: a spinal cord of a patient, or one of a peripheral nerve or a nerve root of the patient, and wherein the second target tissue is associated with one of: the spinal cord of the patient, or one of the peripheral nerve or the nerve root of the patient;
      control sensing circuitry to detect, via an electrode combination at the second target tissue, an evoked compound action potential (ECAP) signal elicited by a first electrical stimulation pulse of the first train of electrical stimulation pulses to the first target tissue;
      determine a timing of the detection of the ECAP signal; and
      determine, based on the timing of the detection of the ECAP signal, a timing of delivery of subsequent electrical stimulation pulses of the first train of electrical stimulation pulses with respect to delivery of subsequent electrical stimulation pulses of the second train of electrical stimulation pulses.

2. The medical device of claim 1, wherein the first frequency for the first train of pulses is selected from a frequency range from approximately 900 Hz to approximately 1200 Hz.

3. The medical device of claim 1, wherein the first frequency for the first train of pulses is selected from a frequency range from approximately 130 Hz to approximately 600 Hz.

4. The medical device of claim 1, wherein the second frequency for the second train of pulses is selected from a frequency range from approximately 10 Hz to approximately 60 Hz.

5. The medical device of claim 1, wherein the first train of electrical stimulation pulses has an amplitude below a perception threshold of the patient.

6. The medical device of claim 1, wherein the second train of electrical stimulation pulses has an amplitude below a perception threshold of the patient.

7. The medical device of claim 1, wherein the first target tissue comprises glial cells, and wherein the second target tissue comprises neurons.

8. The medical device of claim 1, wherein the first target tissue comprises the spinal cord, and wherein the second target tissue comprises at least one of the peripheral nerve or the nerve root.

9. The medical device of claim 8, wherein the second target tissue comprises the peripheral nerve.

10. The medical device of claim 1, further comprising the stimulation generation circuitry.

11. The medical device of claim 1, wherein the first target tissue comprises at least one of the peripheral nerve or the nerve root, and wherein the second target tissue comprises the spinal cord of the patient.

12. The medical device of claim 11, wherein the first target tissue comprises the peripheral nerve.

13. The medical device of claim 1, further comprising the sensing circuitry.

14. A computer-readable storage medium comprising instructions that, when executed, cause the processing circuitry to:

control stimulation generation circuitry to:

generate a first train of electrical stimulation pulses at a first frequency to a first target tissue; and generate a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, wherein at least the first target tissue is associated with one of: a spinal cord of a patient, or one of a peripheral nerve or a nerve root of the patient, and wherein the second target tissue is associated with one of: the spinal cord of the patient, or one of the peripheral nerve or the nerve root of the patient;

control sensing circuitry to detect, via an electrode combination at the second target tissue, an evoked compound action potential (ECAP) signal elicited by a first electrical stimulation pulse of the first train of electrical stimulation pulses to the first target tissue;

determine a timing of the detection of the ECAP signal; and determine, based on the timing of the detection of the ECAP signal, a timing of delivery of subsequent electrical stimulation pulses of the first train of electrical stimulation pulses with respect to delivery of subsequent electrical stimulation pulses of the second train of electrical stimulation pulses.

15. A method comprising:

generating, by stimulation generation circuitry, a first train of electrical stimulation pulses at a first frequency to a first target tissue; and generating, by the stimulation generation circuitry, a second train of electrical stimulation pulses at a second frequency to a second target tissue different from the first target tissue, wherein at least some electrical stimulation pulses of the first train of electrical stimulation pulses are interleaved with at least some electrical stimulation pulses of the second train of electrical stimulation pulses, wherein at least the first target tissue is associated with one of: a spinal cord of a patient, or one of a peripheral nerve or a nerve root of the patient, and wherein the second target tissue is associated with one of: the spinal cord of the patient, or one of the peripheral nerve or the nerve root of the patient;

controlling, by processing circuitry, sensing circuitry to detect, via an electrode combination at the second target tissue, an evoked compound action potential (ECAP) signal elicited by a first electrical stimulation pulse of the first train of electrical stimulation pulses to the first target tissue;

determining, by the processing circuitry, a timing of the detection of the ECAP signal; and determining, by the processing circuitry and based on the timing of the detection of the ECAP signal, a timing of delivery of subsequent electrical stimulation pulses of the first train of electrical stimulation pulses with respect to delivery of subsequent electrical stimulation pulses of the second train of electrical stimulation pulses.

16. The method of claim 15, wherein the first frequency for the first train of pulses is selected from a frequency range from approximately 900 Hz to approximately 1200 Hz.

17. The method of claim 15, wherein the first frequency for the first train of pulses is selected from a frequency range from approximately 130 Hz to approximately 600 Hz.

18. The method of claim 15, wherein the second frequency for the second train of pulses is selected from a frequency range from approximately 10 Hz to approximately 60 Hz.

19. The method of claim 15, wherein the first train of electrical stimulation pulses has an amplitude below a perception threshold of the patient.

20. The method of claim 15, wherein the second train of electrical stimulation pulses has an amplitude below a perception threshold of the patient.

21. The method of claim 15, wherein the first target tissue comprises glial cells, and wherein the second target tissue comprises neurons.

22. The method of claim 15, wherein the first target tissue comprises the spinal cord, and wherein the second target tissue comprises at least one of the peripheral nerve or the nerve root.

23. The method of claim 15, wherein the first target tissue comprises at least one of the peripheral nerve or the nerve root, and wherein the second target tissue comprises the spinal cord of the patient.

* * * * *